(12) United States Patent
Lagree

(10) Patent No.: US 10,500,441 B2
(45) Date of Patent: Dec. 10, 2019

(54) PILATES EXERCISE ROUTINE SYSTEM AND METHOD

(71) Applicant: Lagree Technologies, Inc., Burbank, CA (US)

(72) Inventor: Sebastien Anthony Louis Lagree, West Hollywood, CA (US)

(73) Assignee: Lagree Technologies, Inc., Burbank, CA (US)

( * ) Notice: Subject to any disclaimer, the term of this patent is extended or adjusted under 35 U.S.C. 154(b) by 366 days.

(21) Appl. No.: 14/613,779

(22) Filed: Feb. 4, 2015

(65) Prior Publication Data

US 2015/0217164 A1 Aug. 6, 2015

Related U.S. Application Data

(60) Provisional application No. 61/935,432, filed on Feb. 4, 2014.

(51) Int. Cl.
| | | |
|---|---|---|
| *A63B 24/00* | (2006.01) | |
| *A63B 22/00* | (2006.01) | |
| *G06F 19/00* | (2018.01) | |
| *A63B 21/02* | (2006.01) | |
| *H04M 1/725* | (2006.01) | |

(52) U.S. Cl.
CPC ...... *A63B 24/0075* (2013.01); *A63B 22/0023* (2013.01); *A63B 22/0089* (2013.01); *A63B 24/0062* (2013.01); *A63B 24/0087* (2013.01); *G06F 19/3481* (2013.01); *A63B 21/023* (2013.01); *A63B 2024/0065* (2013.01); *A63B 2024/0093* (2013.01); *A63B 2220/30* (2013.01); *A63B 2225/15* (2013.01); *A63B 2225/20* (2013.01); *A63B 2225/50* (2013.01); *A63B 2230/045* (2013.01); *A63B 2230/105* (2013.01); *A63B 2230/305* (2013.01); *A63B 2230/605* (2013.01); *A63B 2230/75* (2013.01); *H04M 1/72522* (2013.01)

(58) Field of Classification Search
CPC .............. G09B 19/003; A63B 24/0075; A63B 24/0062; A63B 24/0087; A63B 22/0023; A63B 22/0089; A63B 21/023; A63B 2024/0065; A63B 2024/0093; A63B 2220/30; A63B 2225/15; A63B 2225/20; A63B 2225/50; A63B 2230/045; A63B 2230/105; A63B 2230/305; A63B 2230/605; A63B 2230/75; G06F 19/3481; H04M 1/72522
USPC ......................................................... 434/247
See application file for complete search history.

(56) References Cited

U.S. PATENT DOCUMENTS

| | | | |
|---|---|---|---|
| 3,770,267 | A | 11/1973 | McCarthy |
| 5,066,005 | A | 11/1991 | Luecke |
| 7,163,500 | B2 | 1/2007 | Endelman |
| 7,803,095 | B1 | 9/2010 | Lagree |
| 7,811,201 | B1 * | 10/2010 | Mikan ................ A63B 24/0062 |
| | | | 482/4 |

(Continued)

*Primary Examiner* — Corbett B Coburn
(74) *Attorney, Agent, or Firm* — Neustel Law Offices

(57) ABSTRACT

A Pilates Exercise System. A member ID of a member of the Pilates exercise system is received. A selection of a Pilates exercise routine comprising of two or more Pilates exercises is received. Settings associated with a previous performance of at least one of the two or more exercises by the member are provided.

20 Claims, 6 Drawing Sheets

(56) References Cited

U.S. PATENT DOCUMENTS

| | | | |
|---|---|---|---|
| 2003/0119635 A1* | 6/2003 | Arbuckle | A63B 22/0087 482/142 |
| 2007/0033069 A1* | 2/2007 | Rao | A63B 24/00 705/2 |
| 2007/0219059 A1* | 9/2007 | Schwartz | A61B 5/0205 482/8 |
| 2008/0096726 A1* | 4/2008 | Riley | A63B 24/0006 482/8 |
| 2009/0192021 A1* | 7/2009 | Wu | A61H 1/005 482/4 |
| 2010/0227748 A1 | 9/2010 | Campanaro | |
| 2011/0159469 A1* | 6/2011 | Hwang | A61B 5/222 434/247 |
| 2012/0077641 A1* | 3/2012 | Dyer | A63B 22/00 482/8 |
| 2012/0172176 A1* | 7/2012 | Zhang | A63B 71/0054 482/8 |
| 2012/0237910 A1* | 9/2012 | Blum | A63B 6/00 434/247 |
| 2012/0295771 A1 | 11/2012 | Lagree | |
| 2013/0095978 A1* | 4/2013 | Sauter | A63B 24/0087 482/4 |
| 2014/0121076 A1 | 5/2014 | Lagree | |
| 2014/0121078 A1 | 5/2014 | Lagree | |
| 2014/0121079 A1 | 5/2014 | Lagree | |
| 2014/0212855 A1* | 7/2014 | Robinson | G09B 19/00 434/247 |
| 2015/0024914 A1 | 1/2015 | Lagree | |

* cited by examiner

| MEMBER EXERCISE RECORD | | | | | | | |
|---|---|---|---|---|---|---|---|
| Member ID: | XXXX | | | | | | |
| Routine ID: | YYYY | Date: | 01/01/2014 | | Date Last Run: | 12/15/2013 | |
| Exercise # | Name | Duration | Resistance | Incline | Intensity | Velocity | Heart Rate | Calories |
| 1 | Adductor | 3:25 | 8 | 0° | 7 | 5 | 105 | 47 |
| 2 | Torso | 2:00 | 5 | 5° | 6 | 5 | 110 | 52 |
| 3 | Adductor | 4:00 | 8 | 0° | 8 | 8 | 130 | 62 |
| 4 | Torso | 3:00 | 7 | 10° | 8 | 7 | 135 | 70 |
| | Total: | 12:25 | 7 | | 7 | | | 231 |

PILATES EXERCISE ROUTINE SYSTEM AND METHOD

CROSS REFERENCE TO RELATED APPLICATIONS

I hereby claim benefit under Title 35, United States Code, Section 119(e) of U.S. provisional patent application Ser. No. 61/935,432 filed Feb. 4, 2014. The 61/935,432 application is currently pending. The 61/935,432 application is hereby incorporated by reference into this application.

BACKGROUND OF THE INVENTION

Pilates is a form of physical exercise in which the exerciser performs particular movements on a Pilates apparatus, usually in a Pilates studio. There are Pilates studios located worldwide that have these Pilates apparatuses where millions of exercisers perform complex routines of exercises under the guide of a trained Pilates instructor.

A Pilates apparatus has a number of moveable and adjustable parts, including adjustable handles, foot bars, resistance springs, pulleys, cables and incline that are customizable. The adjustable apparatus parts are then specifically set up for the exerciser based on the unique needs of each exerciser by the trained Pilates instructor who is familiar with the individual needs of the exerciser who frequents the Pilates studio in which the instructor teaches. However the setup task can become burdensome for an instructor as the number of exercisers grows, because of the time involved and the requirement to remember the settings for each exerciser on each Pilates apparatus.

The setup task becomes even more burdensome for the instructor if an exerciser is visiting a studio from out of town, or is otherwise a first-time attendee to Pilates and the instructor is unfamiliar with the background and fitness of the exerciser.

Burdensome though it may be, failure to properly set up the Pilates apparatus could result in inefficient workouts and could even endanger the exerciser. Further, a first-time attendee may require extra attention from the instructor, which could reduce the quality of the workouts of other exercisers in the studio who may require the instructor's attention as well.

BRIEF SUMMARY OF THE INVENTION

A Pilates Exercise System. A member ID of a member of the Pilates exercise system is received. A selection of a Pilates exercise routine comprising of two or more Pilates exercises is received. Settings associated with a previous performance of at least one of the two or more exercises by the member are provided.

There has thus been outlined, rather broadly, some of the features of the invention in order that the detailed description thereof may be better understood, and in order that the present contribution to the art may be better appreciated. There are additional features of the invention that will be described hereinafter and that will form the subject matter of the claims appended hereto. In this respect, before explaining at least one embodiment of the invention in detail, it is to be understood that the invention is not limited in its application to the details of construction or to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DETAILED DESCRIPTION OF THE INVENTION

Figure 1:
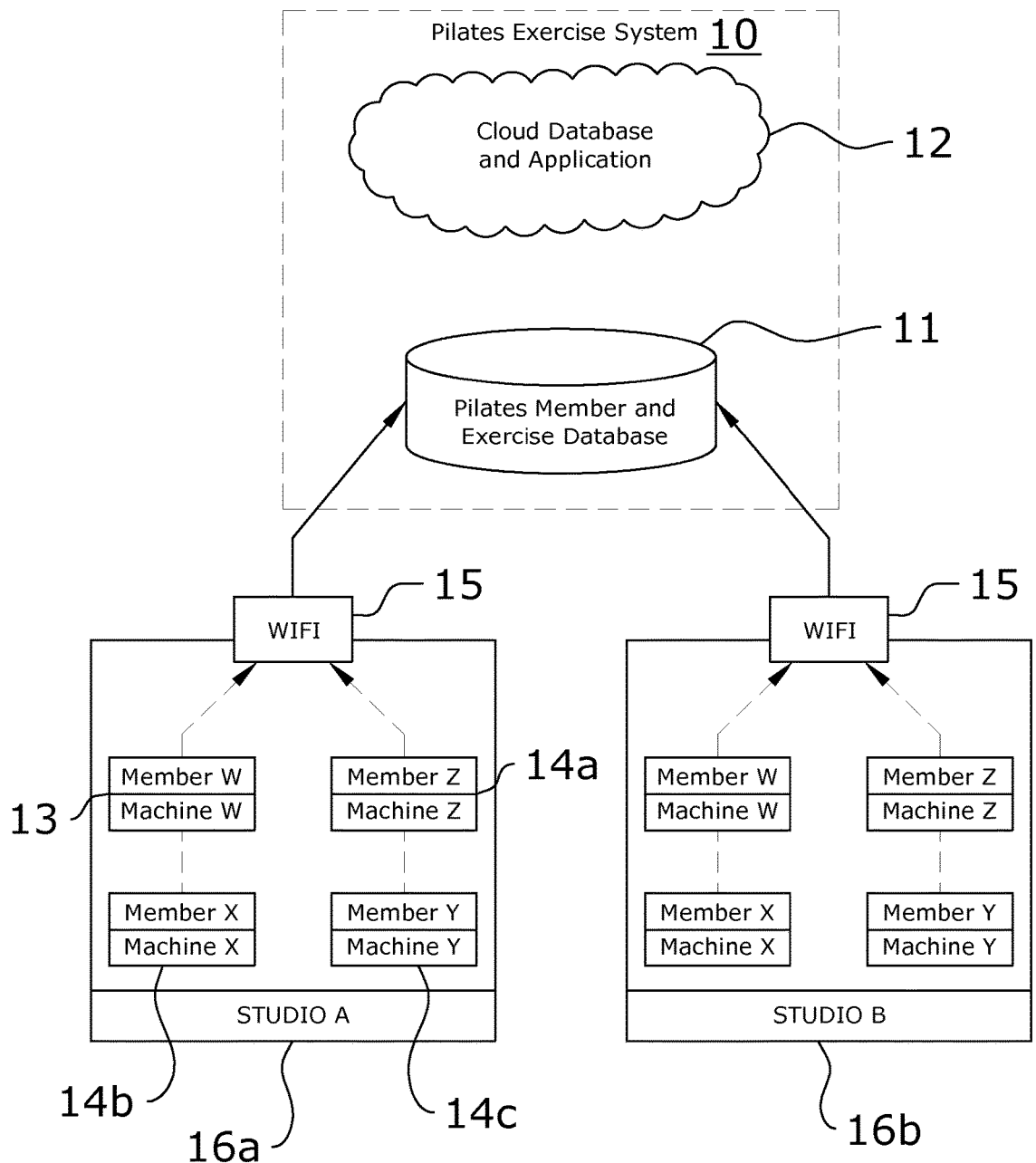
FIG. 1 is an exemplary diagram showing an upper perspective view of the Pilates exercise system.

FIG. 1 is an exemplary diagram showing an upper perspective view of the Pilates exercise system 10. The Pilates exercise system 10 may include a Pilates member database 11 (hereinafter referred to as database 11) which may be accessible through a connection to a server, or may be accessible via the cloud 12. Database 11 may include information about members of the Pilates exercise system 10, including, for example, member IDs, saved exercise routines, and performance data, all which may be accessible via Pilates exercise system 10. A member may be any individual who registers with Pilates exercise system 10, pays a fee, is a member of a studio 16a or 16b that may be a member of the Pilates exercise system 10, or fulfills any other member requirements.

As shown in the example of FIG. 1, two Pilates studios 16a and 16b are shown, each studio 16a, 16b being connected to the Pilates exercise system 10 via a Wi-Fi 15 connection or other type of network connection to access data from database 11. In another embodiment, a portion of the Pilates exercise system 10 may be hosted or provided locally from within a studio 16a or 16b. For example, for those exercisers who regularly attend studio 16a, their information may be stored locally at studio 16a, and may be synchronized with database 11.

Member W is shown in studio 16a as performing a Pilates exercise on a corresponding Machine W as illustrated in box 13. Other Members X, Y and Z are shown as performing Pilates exercises on different Machines X, Y, Z within the same studio 16a as illustrated in boxes 14a, 14b, 14c. The number of machines and members shown are exemplary only and are not limiting of the invention which may have more or less members and machines.

Member W is also shown in studio 16b as performing a Pilates exercise on Machine W. In the example shown, Member W may be a regular with studio 16a, but may be out of town and visiting studio 16b. In studio 16b, Member W performs Pilates exercises on Machine W, which is different from Machine W in studio 16a. In order to properly perform the same exercises, without use of Pilates exercise system 10, Member W would need to manually write down or try and remember all the settings and exercises that were previously performed in studio 16a.

However, through the connection with Pilates exercise system 10, Member W at studio 16b is able to access their member profile and Pilates exercise information stored on Pilates member database 11, even though it may have been established or updated while at studio 16a. Through accessing their personal data from database 11, Member W may perform their workout at studio 16b, and their profile may be updated based on data collected during their workout on Machine W. For example, their performance data while exercising at studio 16b may be uploaded to database 11. Then, if Member W returns to studio 16a or visits another connected studio or another non-connected studio but using a connected device 40 (such as a smartphone), Member W will have access to their most recent workout data and profile data through Pilates exercise system 10.

In an embodiment, a member may have access to Pilates exercise system 10 through the use of a smartphone. For example, the smartphone may have an app or may be able to connect to Pilates exercise system 10 through the Internet. For convenience, member data may be stored both locally on the smartphone and in database 11, thereby allowing members access to their data even during times of poor reception. The data may occasionally be synchronized between the smartphone and database 11 during times of connectivity. In another embodiment, particular Pilates apparatuses or displays near a Pilates apparatus within a studio 16a, 16b may be connected to Pilates exercise system 10.

Pilates exercise system 10 allows members, no matter where they are, to access their exercise information, modify their routines, watch instructional videos, and track or compare their past performance of exercise routines.

Figure 2:
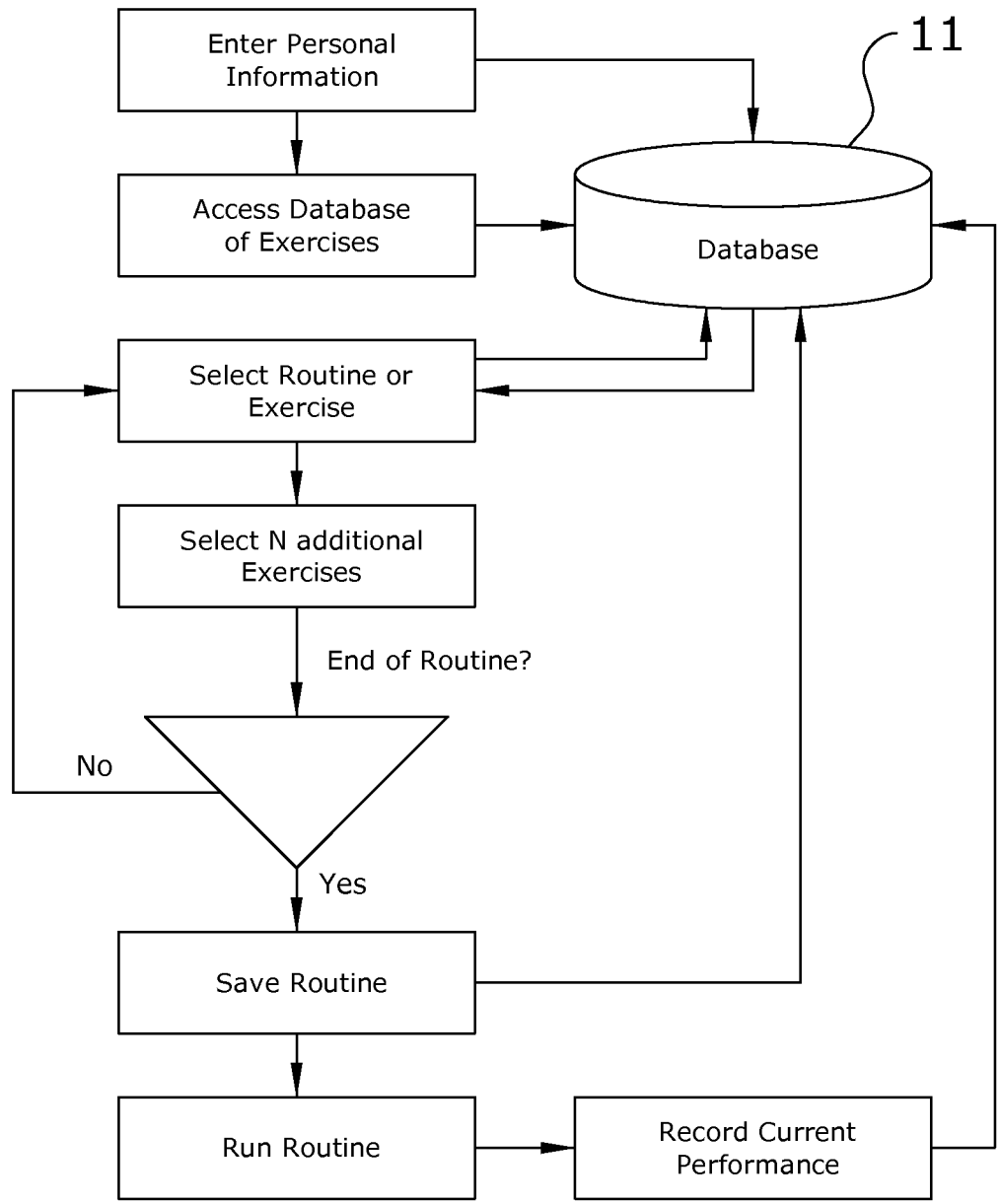
FIG. 2 is an exemplary flow chart illustrating the creation of a member profile, according to an embodiment.

FIG. 2 is an exemplary flow chart illustrating the creation of a member profile, according to an embodiment. A user begins by connecting to the Pilates exercise system 10 and entering personal information to create a user profile. The user profile is downloaded to an exercise machine prior to starting an exercise. Using the downloaded user profile, the exercise machine knows the history for the user and can automatically adjust the settings of the exercise machine accordingly. The personal information entered for the user profile may include, but is not limited to, name, age, gender, fitness level, height, weight, past injuries, fitness goals, perceived fitness level, and other information that may be helpful in determining the fitness of a member/exerciser. The fitness level may be an indication of recent or past history as to how the member performed one or more exercises. For example, fitness level may indicate a maximum bench press, the time to run one mile, a heart rate after exercising for a specified amount of time, a weight and number of reps of an exercise, or other similar information.

This information may be used to track the member's progress over time. For example, the member's weight at profile creation may be compared to the member's weight at a later point in time. In an embodiment, a member may also select or provide a username and/or password by which to access the Pilates exercise system 10.

Once registered, the member may have access to the multi-media database 11 which may include a number of Pilates exercises and/or routines. A Pilates exercise may be an individual exercise on a Pilates apparatus, while a routine may be two or more Pilates exercises grouped together to achieve specific results (as used herein, exercise and routine are used interchangeably unless otherwise specified).

The Pilates exercises to which the members have access via database 11 may include various information that may enable the member to properly perform the exercise. This information may include, but is not limited to, instructional multimedia on how to set up and/or perform the exercise, an indication as to what the specific results intended to be achieved by the exercise (e.g., which body part(s) are targeted, endurance, power, etc.), how many other users have selected this exercise as part of their routines, or what other exercises could be performed in addition to or in lieu of the selected exercise.

The member may select any exercises from database 11 that are of interest to the member to assemble one or more customized exercise routines. The routines and exercises may then be used immediately or later accessed by the member while exercising in a studio 16a, 16b.

While or after the member performs one or more exercises, Pilates exercise system 10 may collect performance data related to the exercises performed. The performance data may be recorded or measured by a mobile device, the Pilates apparatus, manual entry and recordation by the user, input from an instructor, or any other means. The performance data may include, but is not limited to, the date, the duration of the exercises performed, the workout intensity level, blood pressure, pulse, respiration, energy output (e.g. in watts), special adjustments to the apparatus or any other information that may be useful in measuring a member's fitness or performance level.

Figure 3:
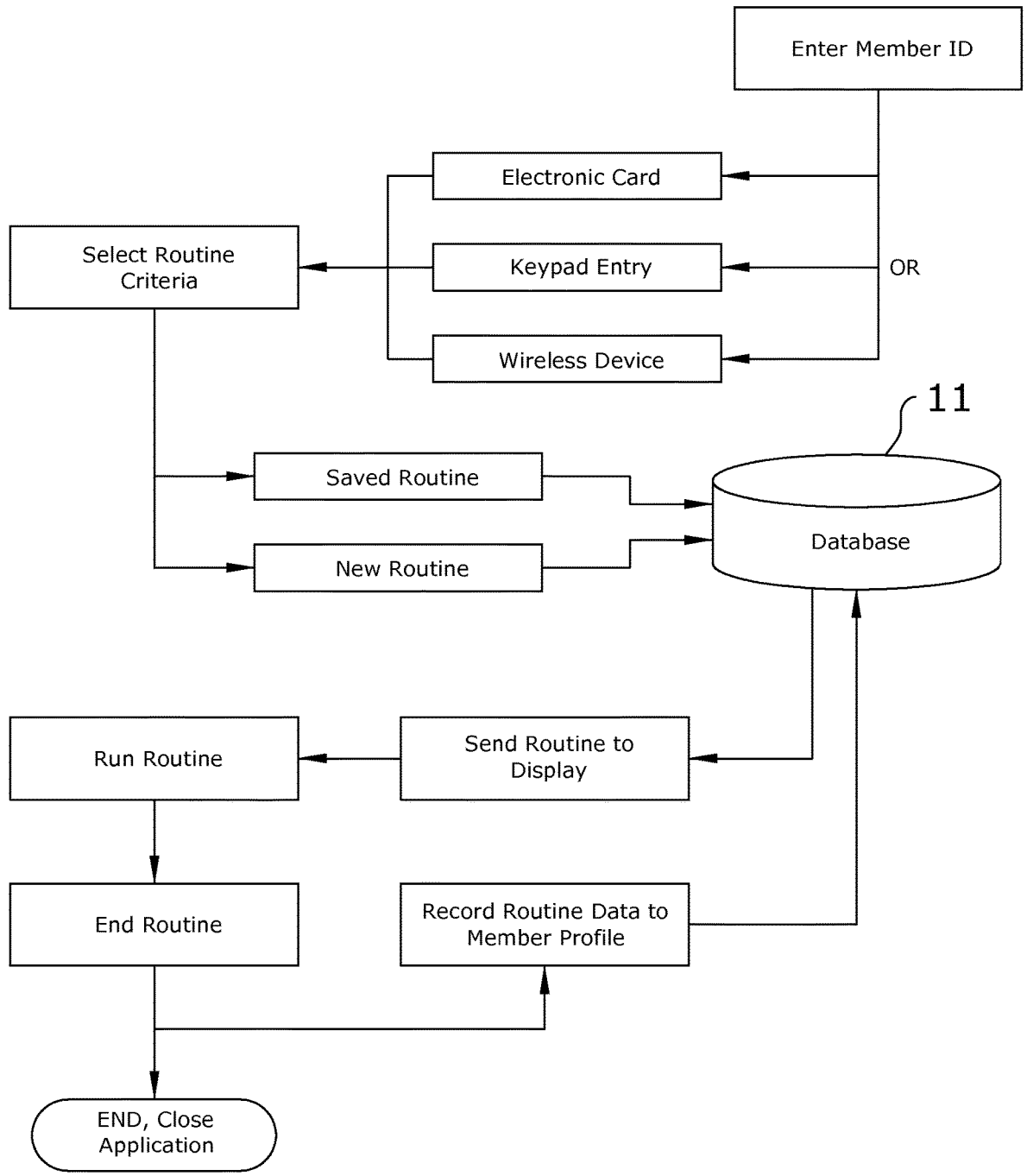
FIG. 3 is an exemplary flow chart illustrating a member accessing their member profile, according to an embodiment.

FIG. 3 is an exemplary flow chart illustrating a member accessing their member profile, according to an embodiment. Each member may have a member ID. The member ID may be a unique identifier assigned to the member, a name or username provided by the member, a phone number, or other identifier. In an embodiment, if member is accessing Pilates exercise system 10 from a mobile device, the member ID may be retrieved from an app on the device or the mobile number.

In an embodiment, a member may log into or access the Pilates exercise system 10 from a Pilates apparatus or display device located in a proximity to a Pilates apparatus. In an embodiment, the member may access Pilates exercise system 10 by entering a unique ID on a keypad, or through use of an electronic card or biometric identifier.

Through whatever device the member uses to access the Pilates exercise system 10, the member may request and retrieve previously stored or selected exercises or routines, or select new exercises to perform. In an embodiment, Pilates exercise system 10 may provide the member with routines that are generally selected by members with a similar age, weight, and/or fitness level as the member.

For new exercises, the Pilates exercise system 10 may provide the user with an option to view an instructional video on how to perform the exercise. The member may then run the selected exercise(s) until complete or until the member decides to stop exercising. During the performance of the exercise(s) the device through which the member is accessing the Pilates exercise system 10 may be capturing, monitoring, or recording performance data, including video, or the member's performance. The performance data may then be stored with the member profile in the database 11. Additionally, the member or instructor may enter notes pertaining to the performance of the exercises that may be later accessed.

Figures 4, 5:
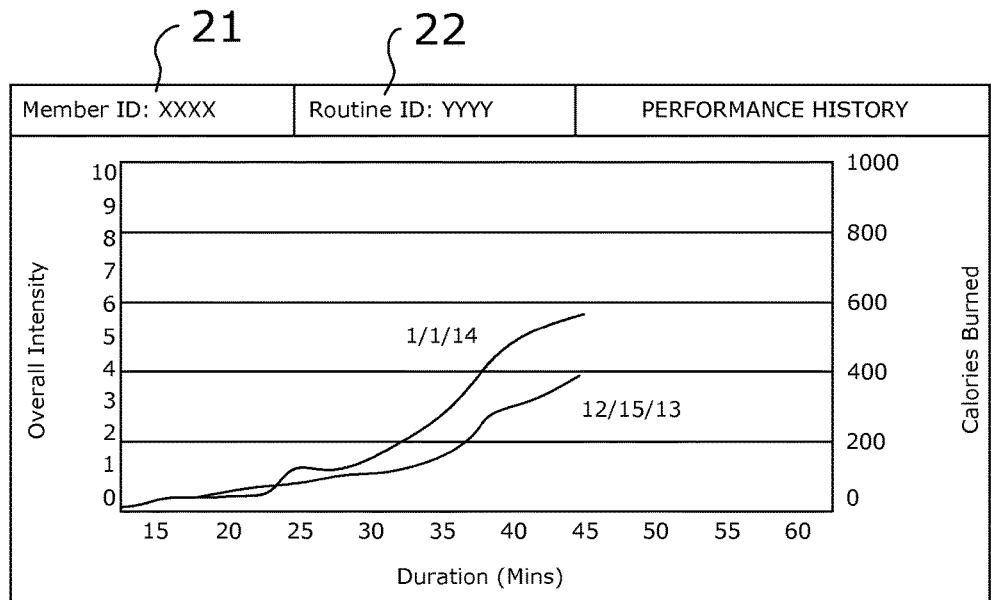
FIG. 4 is an example table of database that may be used to record member performance data, according to an embodiment.
FIG. 5 is an exemplary diagram showing a performance trend, according to an embodiment.

FIG. 4 is an example table 20 of database 11 that may be used to record member performance data, according to an embodiment. Table 20 is an example of a table that may be used in database 11 to capture or store performance data and/or workout routines of a member.

Table 20 may include the member ID 21 of the member for whose data is being shown. In the example shown, the member ID 21 is XXXX. As noted above, member ID 21 may be a member's name, special ID, username, initials, or any other member identifier.

Table 20 may also include a name or ID of the routine 22. In the example shown, the routine may be named YYYY. The routine ID 22 may be provided by the member or by Pilates exercise system 10. For example, any preconfigured routines provided by Pilates exercise system 10 and selected by a member, may have a preconfigured, which may be modifiable by the member.

The table 20 includes a exercise number column that indicates the order in which the exercise are or were performed during the course of the routine, and next to each exercise number is the name of the exercise. In the example shown, the same two exercises are repeated during the course of the routine, but other routines may include any number of unique exercises.

In addition to providing the routine information, table 20 also includes exemplary performance data that may have been stored or captured with regard to a performance of the routine by the member. Table 20 provides dates 23A and 23B. Date 23A may be a date of a most recent performance of the routine, while date 23B is a date of a prior performance before date 23A. In another embodiment, table 20 may include a date on which the routine was selected (if it was a preconfigured routine) or was last modified or created, and the number of times the routine has been run by member.

Table 20 may include individual performance data, such as duration, intensity, velocity, heart rate, and calorie information. A duration column indicates how long it took the member to complete the exercise during the course of the routine. The intensity column may indicate an intensity of the performance of the exercise, while velocity indicates a speed at which the exercise was performed. The heart rate of the member and a number of calories burned during the exercise may be stored, which may captured, for example, by the Pilates apparatus or other device.

A resistance level (e.g., spring resistance) column and an incline column may indicate the settings (or recommended settings) on the Pilates apparatus during a performance of the exercise. In other embodiments, table 20 may include data different from that described with FIG. 4.

FIG. 5 is an exemplary diagram showing a performance trend, according to an embodiment. The graph 30 shows the differences in the physical performance between of a Pilates exercise routine (YYYY) as performed by a member (XXXX) during two different exercise sessions.

Graph 30 includes a duration measure along the X-axis, and an overall intensity and number of calories burned along the Y-axis. These are exemplary, and other performance charts may include different measures and may be displayed different ways. For example, a pie chart may be used to compare the number of calories burned during any number of different exercise dates. As may be seen in the example of FIG. 5, there was an improvement in intensity and calories burned between the Dec.15, 2013 performance and the Jan. 1, 2014 performance. This improvement in performance may then be used to suggest new exercises for the member, new intensity/velocity goals, or other adjustments that may be made. Similarly, if the performance of the member decreased, other adjustments to the recommended exercises may be made.

Though the example of FIG. 5 shows a comparison of two workouts of the same routine, in another embodiment, graph 30 may show differences between two different workout routines. This may be used, for example, to determine which routine is more effective (e.g., in burning calories) to help the member reach their goals. Or, for example, two members may compare their performance of a routine against each other.

Figure 6:
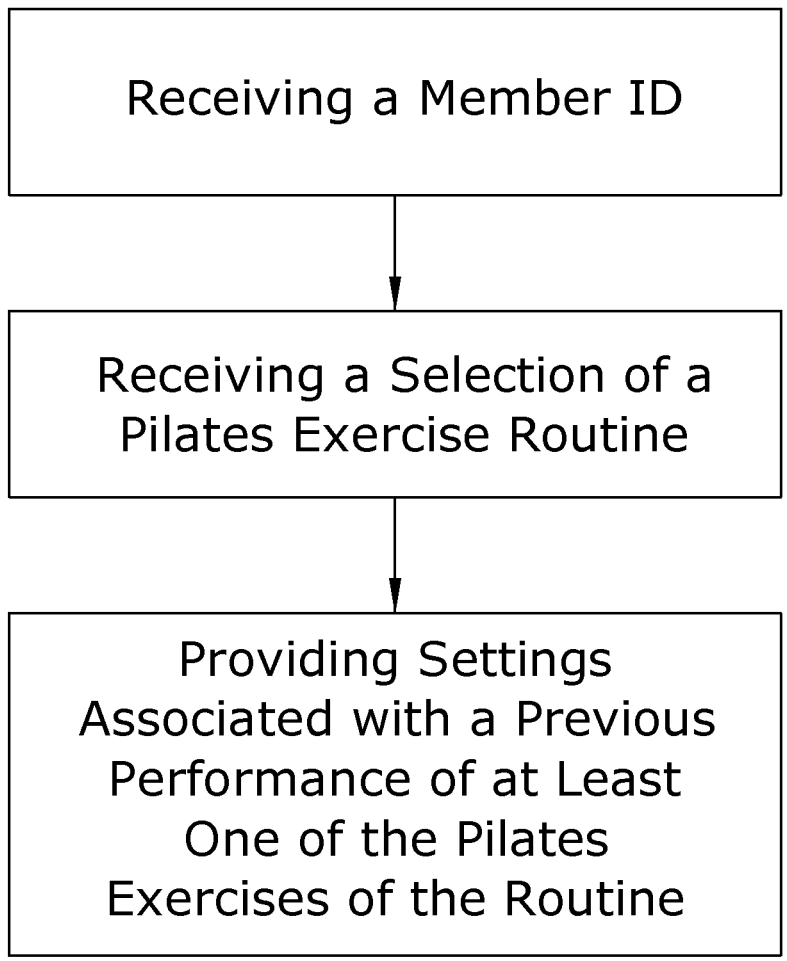
FIG. 6 is an exemplary flow chart illustrating an operation of the Pilates exercise system, according to an embodiment.

FIG. 6 is an exemplary flow chart illustrating an operation of the Pilates exercise system 10, according to an embodiment. The Pilates exercise system 10 may receive a request to login, from a member. As part of the login, the member may be required to provide a member ID (and password).

The member may already have a profile created within Pilates exercise system 10. Pilates exercise system 10 may receive a selection of one or more exercises for a Pilates exercise routine for the member. In an embodiment, the Pilates exercise system 10 may recommend or provide Pilates exercises from which the member or an instructor may choose. In an embodiment, a member may create a new routine using one or more exercises that were previously performed by the member.

Pilates exercise system 10 may then provide settings that are associated with a performance of the exercises. The settings may include, for example, an incline that was previously used by the member in performing the exercise, or a suggested incline if the member has not performed the exercise before. Other settings information may be provided as well, depending on the individual needs of the member.

Figure 7:
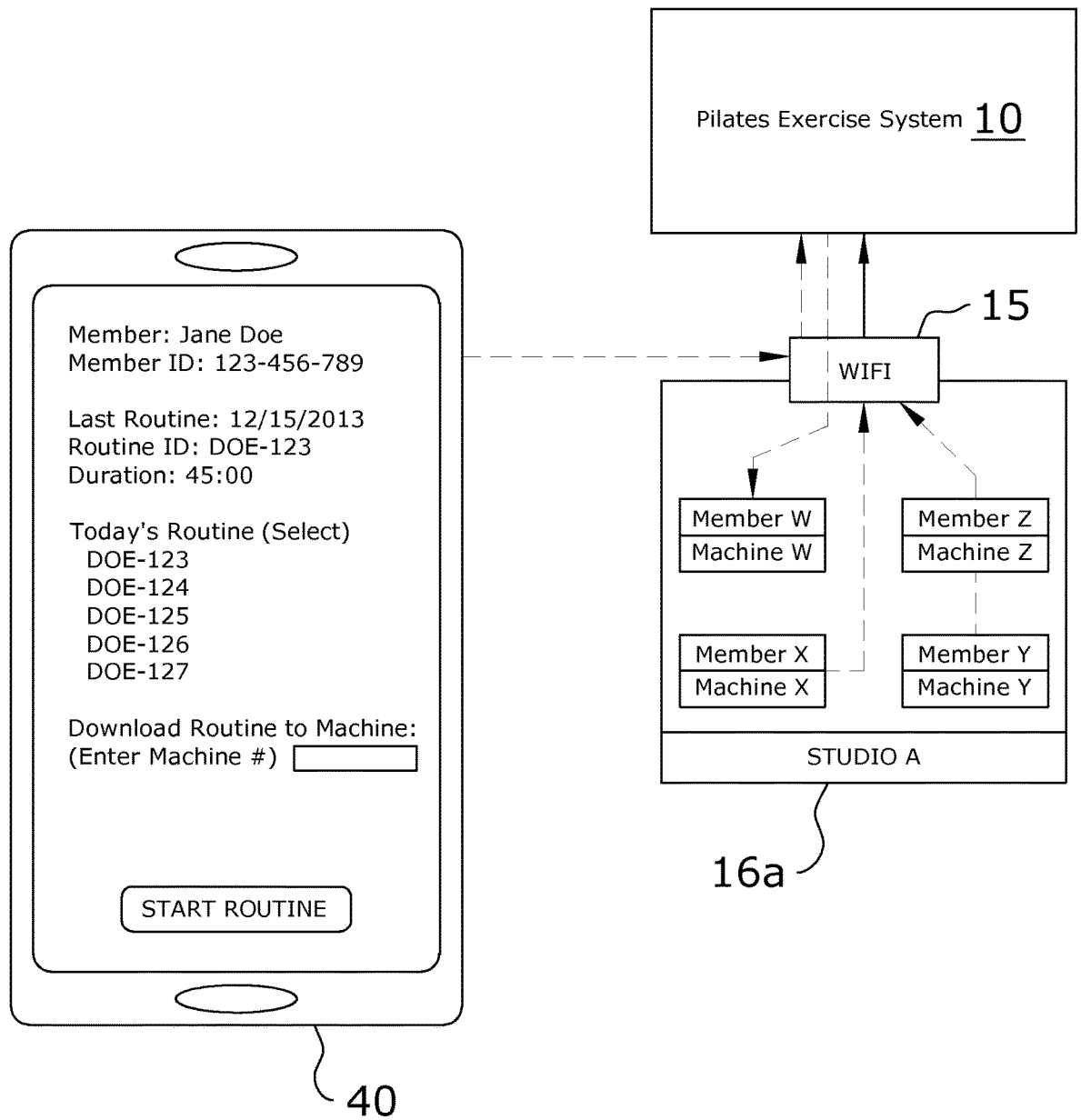
FIG. 7 is an exemplary embodiment of the Pilates exercise system.

FIG. 7 is an exemplary embodiment of the Pilates exercise system 10. A mobile device 40 communicates with the Pilates exercise system 10. Mobile device 40 may include a smartphone, touchpad, laptop, or any other mobile electronic communication device configured to communication over a wired/wireless network with Pilates exercise system 10.

In an embodiment, mobile device 40 may be pre-authorized to access Pilates exercise system 10. For example, mobile device 40 may have a phone number that corresponds to a member. Or, for example, mobile device 40 may have an app or application installed on it through which a member may access Pilates exercise system 10. A member may need to login to their account through mobile device 40 in order to access Pilates exercise system 10 (which may include any local data or functionality available through mobile device 40).

Through mobile device 40, a member may interact with data from Pilates exercise system 10. For example, the member may access their workout routines as shown in the example of FIG. 7, or instructional videos on how to perform various Pilates exercises. As shown, mobile device 40 may be in communication with Pilates exercise system 10 either through a cellular network, or through the Wifi 15 of studio 16a.

In an embodiment, mobile device 40 may store member information locally, so that member may have access to Pilates exercise system 10 even during times of limited/no connectivity. Member may update the data locally (e.g., such as performance data, changing routines, etc.), and Pilates exercise system 10 may occasionally synchronize with mobile device 40. In an embodiment, any functionality described herein through Pilates exercise system 10 may be performed via mobile device 40 that is authorized or otherwise configured to access Pilates exercise system 10.

The software application will communicate directly to the exercise equipment to control all the settings of the exercise equipment including, but not limited to, resistance, machine incline/decline, side rotation of the machine, change in attitude of machine, handle bars rotating in the correct position, and speed for the carriage. For example, the instructor may set up the following sequence of exercises to be played on all the exercise equipment devices: 1) Elevator Lunge, Right leg, which requires 1 yellow spring (light resistance) immediately followed by 2) skating, right leg, which requires 1 Red and 1 Yellow springs (heavy resistance). The software automatically adds the red spring for the skating exercise and depending on the continuation of the routine will continue to add or reduce tension without the exerciser having to adjust their own tension.

Each exerciser will have a profile which will be downloaded to the exercise equipment and interact with the software described above, so let's say that a user is doing the same sequence of movements: 1) Elevator Lunge, Right leg, which requires 1 yellow spring (light resistance) immediately followed by 2) Skating, Right leg, which requires 1 Red and 1 Yellow springs (heavy resistance). The software will automatically add the Red spring for the Skating Exercise and depending on the continuation of the routine will continue to add or reduce tension without the participant having to adjust their own tension similar to the above process discussed. However, in this embodiment, the exercise machine also accesses your history of workouts in the user's database profile and determines that the user has done 9 sessions already in the past 3 weeks, so the exercise machine decides to add one extra yellow spring as well as the Red to keep the tension effective, so the machine now has 1 Red and 2 Yellow springs (extra heavy resistance).

Other adjustments made by the machine will be based on heart rate variability (HRV), brain activity, muscle stimulation and other physiological measurements. If the machine recognizes that the exerciser is not working at their full potential, the exercise machine will add stress to your body (e.g. increase the incline, increase the spring tension, rotate the machine to a side). Alternatively, if the exerciser is working at a higher level than they should, the exercise machine will reduce the stress on the exerciser (e.g. reduce the incline, reduce the spring tension, level the exercise machine). The same applies to the elevation of the ramp, so if the exercise is too easy for an exerciser, the machine will automatically increase the level of the ramp and without asking the user but will tell the user a message such as "Alex, how about going up one extra level for this one?" The user can override the suggestions of the equipment to prevent the increase (or decrease) in stress.

In your profile setting, the user will be able to choose how aggressive or hard they want the machine to be during exercises. For example, a user could select "drill sergeant" if they want the machine to make more aggressive or stronger setting. Alternatively, the user could select "care bear" and have the machine only suggest you to push more but not to actually make the changes for you automatically. The software application will also help users with their form and help correct any poor form and posture. The software application will also tell people to slow down and help people to slow down even more over the course of several workouts.

The present invention may be utilized upon any telecommunications network capable of transmitting data including voice data and other types of electronic data. Examples of suitable telecommunications networks for the present invention include but are not limited to global computer networks (e.g. Internet), wireless networks, cellular networks, satellite communications networks, cable communication networks (via a cable modem), microwave communications networks, local area networks (LAN), wide area networks (WAN), campus area networks (CAN), metropolitan-area networks (MAN), and home area networks (HAN). The present invention may communicate via a single telecommunications network or multiple telecommunications networks concurrently. Various protocols may be utilized by the electronic devices for communications such as but not limited to HTTP, SMTP, FTP and WAP (wireless Application Protocol). The present invention may be implemented upon various wireless networks such as but not limited to 3G, 4G, LTE, CDPD, CDMA, GSM, PDC, PHS, TDMA, FLEX, REFLEX, IDEN, TETRA, DECT, DATATAC, and MOBITEX. The present invention may also be utilized with online services and Internet service providers.

The Internet is an exemplary telecommunications network for the present invention. The Internet is comprised of a global computer network having a plurality of computer systems around the world that are in communication with one another. Via the Internet, the computer systems are able to transmit various types of data between one another. The communications between the computer systems may be accomplished via various methods such as but not limited to wireless, Ethernet, cable, direct connection, telephone lines, and satellite.

The mobile device or smartphone described herein may be comprised of any type of computer for practicing the various aspects of the present invention. For example, the mobile device can be a personal computer (e.g. APPLE® based computer, an IBM based computer, or compatible thereof) or a tablet computer (e.g. IPAD®). The mobile device may also be comprised of various other electronic devices capable of sending and receiving electronic data including but not limited to smartphones, mobile phones, telephones, personal digital assistants (PDAs), mobile electronic devices, handheld wireless devices, two-way radios, smart phones, communicators, video viewing units, television units, television receivers, cable television receivers, pagers, communication devices, and digital satellite receiver units.

The mobile device may be comprised of any conventional computer. A conventional computer preferably includes a display screen (or monitor), a printer, a hard disk drive, a network interface, and a keyboard. A conventional computer also includes a microprocessor, a memory bus, random access memory (RAM), read only memory (ROM), a peripheral bus, and a keyboard controller. The microprocessor is a general-purpose digital processor that controls the operation of the computer. The microprocessor can be a single-chip processor or implemented with multiple components. Using instructions retrieved from memory, the microprocessor controls the reception and manipulations of input data and the output and display of data on output devices. The memory bus is utilized by the microprocessor to access the RAM and the ROM. RAM is used by microprocessor as a general storage area and as scratch-pad memory, and can also be used to store input data and processed data. ROM can be used to store instructions or program code followed by microprocessor as well as other data. A peripheral bus is used to access the input, output and storage devices used by the computer. In the described embodiments, these devices include a display screen, a printer device, a hard disk drive, and a network interface. A keyboard controller is used to receive input from the keyboard and send decoded symbols for each pressed key to microprocessor over bus. The keyboard is used by a user to input commands and other instructions to the computer system. Other types of user input devices can also be used in conjunction with the present invention. For example, pointing devices such as a computer mouse, a track ball, a stylus, or a tablet to manipulate a pointer on a screen of the computer system. The display screen is an output device that displays images of data provided by the microprocessor via the peripheral bus or provided by other components in the computer. The printer device when operating as a printer provides an image on a sheet of paper or a similar surface. The hard disk drive can be utilized to store various types of data. The microprocessor, together with an operating system, operate to execute computer code and produce and use data. The computer code and data may reside on RAM, ROM, or hard disk drive. The computer code and data can also reside on a removable program medium and loaded or installed onto a computer system when needed. Removable program mediums include, for example, CD-ROM, PC-CARD, USB drives, floppy disk and magnetic tape. The network interface circuit is utilized to send and receive data over a network connected to other computer systems. An interface card or similar device and appropriate software implemented by microprocessor can be utilized to connect the computer system to an existing network and transfer data according to standard protocols.

The invention is described above with reference to block and flow diagrams of systems, methods, apparatuses, and/or computer program products according to example embodiments of the invention. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, or may not necessarily need to be performed at all, according to some embodiments of the invention. These computer-executable program instructions may be loaded onto a general-purpose computer, a special-purpose computer, a processor, or other programmable data processing apparatus to produce a particular machine, such that the instructions that execute on the computer, processor, or other programmable data processing apparatus create means for implementing one or more functions specified in the flow diagram block or blocks. These computer program instructions may also be stored in a computer-readable memory that can direct a computer or other programmable data processing apparatus to function in a particular manner, such that the instructions stored in the computer-readable memory produce an article of manufacture including instruction means that implement one or more functions specified in the flow diagram block or blocks. As an example, embodiments of the invention may provide for a computer program product, comprising a computer usable medium having a computer-readable program code or program instructions embodied therein, said computer-readable program code adapted to be executed to implement one or more functions specified in the flow diagram block or blocks. The computer program instructions may also be loaded onto a computer or other programmable data processing apparatus to cause a series of operational elements or steps to be performed on the computer or other programmable apparatus to produce a computer-implemented process such that the instructions that execute on the computer or other programmable apparatus provide elements or steps for implementing the functions specified in the flow diagram block or blocks. Accordingly, blocks of the block diagrams and flow diagrams support combinations of means for performing the specified functions, combinations of elements or steps for performing the specified functions, and program instruction means for performing the specified functions. It will also be understood that each block of the block diagrams and flow diagrams, and combinations of blocks in the block diagrams and flow diagrams, can be implemented by special-purpose, hardware-based computer systems that perform the specified functions, elements or steps, or combinations of special-purpose hardware and computer instructions.

The present invention may be embodied in other specific forms without departing from the spirit or essential attributes thereof, and it is therefore desired that the present embodiment be considered in all respects as illustrative and not restrictive. Many modifications and other embodiments of the invention will come to mind to one skilled in the art to which this invention pertains and having the benefit of the teachings presented in the foregoing description and the associated drawings. Therefore, it is to be understood that the invention is not to be limited to the specific embodiments disclosed and that modifications and other embodiments are intended to be included within the scope of the appended claims. Although methods and materials similar to or equivalent to those described herein can be used in the practice or testing of the present invention, suitable methods and materials are described above. Thus, the present invention is not intended to be limited to the embodiments shown, but is to be accorded the widest scope consistent with the principles and features disclosed herein.

The invention claimed is:

1. A method comprising:
   receiving a member ID of a member of an exercise system, wherein the member ID is contained within a member database of the exercise system and is associated with personal data related to a fitness level of the member;
   receiving a selection of an exercise routine from within a collection of exercise routines each comprising a sequence of two or more exercises, wherein the exercises are selected based on the fitness level and each is associated with an exercise machine type;
   determining a frequency of past workouts;
   determining settings for an exercise machine of the exercise machine type for a subsequent performance of at least one of the two or more exercises by the member based on the frequency of past workouts and first performance data from a previous performance of at least one of the two or more exercises by the member;
   wherein the first performance data comprises a date, duration of the exercises performed, a workout intensity level, blood pressure, pulse, respiration, or energy output from the previous performance; and
   automatically adjusting settings for the exercise machine in accordance with the settings determined.

2. The method of claim 1, further comprising:
   receiving second performance data of the member recorded during the subsequent performance.

3. The method of claim 2, further comprising:
   providing a comparison of the second performance data of the member recorded during the subsequent performance with the first performance data of the member recorded during the previous performance.

4. The method of claim 2, wherein the second performance data comprises a date of the subsequent performance, a heart rate of the member, and notes provided by an instructor who is different from the member.

5. The method of claim 1, wherein the personal data comprises: age, injuries, fitness goals, and one or more exercises performed during the previous performance.

6. The method of claim 1, further comprising:
providing a video of how to perform the two or more exercises of the routine to an interactive display of the exercise machine.

7. The method of claim 1, wherein the step of determining settings is performed by the exercise machine.

8. A system comprising at least a processor and a non-transitory memory, wherein the processor is configured to:
receive a member ID of a member of an exercise system, wherein the member ID is contained within a member database of the exercise system and is associated with personal data related to a fitness level of the member;
receive a selection of an exercise routine from within a collection of exercise routines each comprising a sequence of two or more exercises, wherein the exercises are selected based on the fitness level and each is associated with an exercise machine type;
determining a frequency of past workouts;
determine settings for an exercise machine of the exercise machine type for a subsequent performance of at least one of the two or more exercises by the member based on the frequency of past workouts and first performance data from a previous performance of at least one of the two or more exercises by the member;
wherein the first performance data comprises a date, duration of the exercises performed, a workout intensity level, blood pressure, pulse, respiration, or energy output from the previous performance; and
automatically adjust settings for the exercise machine in accordance with the settings determined.

9. The system of claim 8, wherein the processor is further configured to:
receive second performance data of the member recorded during the subsequent performance.

10. The system of claim 9, wherein the processor is further configured to:
provide a comparison of the second performance data of the member recorded during the subsequent performance with the first performance data of the member recorded during the previous performance.

11. The system of claim 9, wherein the second performance data comprises a date of the subsequent performance, a heart rate of the member, and notes provided by an instructor who is different from the member.

12. The system of claim 8, wherein the personal data comprises: age, injuries, fitness goals, and one or more exercises performed during the previous performance.

13. The system of claim 8, wherein the processor is further configured to:
provide a video of how to perform the two or more exercises of the routine to an interactive display of the exercise machine.

14. The system of claim 8, wherein the exercise machine comprises a processor that is configured to determine settings for the exercise machine that comprises it for a subsequent performance of at least one of the two or more exercises by the member based on a previous performance of at least one of the two or more exercises by the member.

15. A non-transitory computer readable storage medium having a plurality of instructions stored thereon that, when executed by one or more processors, cause the one or more processors to:
receive a member ID of a member of an exercise system, wherein the member ID is contained within a member database of the exercise system and is associated with personal data related to a fitness level of the member;
receive a selection of an exercise routine from within a collection of exercise routines each comprising a sequence of two or more identified exercises, wherein the exercises are selected based on the fitness level and each is associated with an exercise machine type;
determining a frequency of past workouts;
determine settings for an exercise machine of the exercise machine type for a subsequent performance of at least one of the two or more exercises by the member based on the frequency of past workouts and first performance data from a previous performance of at least one of the two or more exercises by the member;
wherein the first performance data comprises a date, duration of the exercises performed, a workout intensity level, blood pressure, pulse, respiration, or energy output from the previous performance; and
automatically adjust settings for the exercise machine in accordance with the settings determined.

16. The non-transitory computer readable storage medium of claim 15, wherein the plurality of instructions further comprises instructions that cause the one or more processors to:
receive second performance data of the member recorded during the subsequent performance.

17. The non-transitory computer readable storage medium of claim 16, wherein the plurality of instructions further comprises instructions that cause the one or more processors to:
provide a comparison of the second performance data of the member recorded during the subsequent performance with the first performance data of the member recorded during the previous performance.

18. The non-transitory computer readable storage medium of claim 15, wherein the second performance data comprises a date of the subsequent performance, a heart rate of the member, and notes provided by an instructor who is different from the member.

19. The non-transitory computer readable storage medium of claim 15, wherein the plurality of instructions further comprises instructions that cause the one or more processors to automatically adjust settings for the exercise machine for a subsequent performance of at least one of the two or more exercises by the member.

20. The non-transitory computer readable storage medium of claim 15, wherein the plurality of instructions further comprises instructions that cause the one or more processors to:
provide a video of how to perform the two or more exercises of the routine to an interactive display of the exercise machine.

* * * * *